(12) United States Patent
Yamanouchi et al.

(10) Patent No.: US 6,794,154 B1
(45) Date of Patent: Sep. 21, 2004

(54) REMEDIES FOR KIDNEY DISEASES AND METHOD FOR SCREENING THE SAME

(75) Inventors: Masaya Yamanouchi, Kusatsu (JP); Hiromi Hase, Tokyo-to (JP); Akiko Honda, Toyonaka (JP); Takeshi Sugaya, Itami (JP)

(73) Assignee: Tanabe Seiyaku Co., Ltd., Osaka-fu (JP)

( * ) Notice: Subject to any disclaimer, the term of this patent is extended or adjusted under 35 U.S.C. 154(b) by 0 days.

(21) Appl. No.: 09/979,765

(22) PCT Filed: Mar. 21, 2000

(86) PCT No.: PCT/JP00/01695

§ 371 (c)(1),
(2), (4) Date: Nov. 27, 2001

(87) PCT Pub. No.: WO00/73791

PCT Pub. Date: Dec. 7, 2000

(30) Foreign Application Priority Data

May 27, 1999 (JP) .............................. 11-147635
Sep. 21, 1999 (JP) .............................. 11-266425

(51) Int. Cl.$^7$ .............................................. G01N 33/53
(52) U.S. Cl. ....................................................... 435/7.8
(58) Field of Search .......................................... 435/7.8

(56) References Cited

U.S. PATENT DOCUMENTS 6,353,009 B1 * 3/2002 Fujiwara et al. ............ 514/365
2002/0182197 A1 * 12/2002 Black et al. ................ 424/94.1

FOREIGN PATENT DOCUMENTS

| EP | 604983 A1 | 7/1994 |
| EP | 1043587 A1 | 10/2000 |
| JP | 11-242026 | 9/1999 |

OTHER PUBLICATIONS

Meunier–Durmont et al., "Up–regulation of the xpression of the gene for liver fatty acid–binding protein by long–chain fatty acids" Biochemical Journal 319 (2): 483–87 (1996).*

Jacques H. Veerkamp et al., "Cytoplasmic Fatty Acid–Binding Proteins: Their Structure and Genes", Prog. Lipid Res., vol. 34, No. 1, pp. 17–52 (1995).

Jurgen M. Lehmann et al., An Antidiabetic Thiazolidinedione Is a High Affinity Ligand for Peroxisome Proliferator–activated Receptor γ PPARγ) **, J. Biol. Chem., vol. 270, No. 22, pp. 12953–12956 (1995).

Timothy M. Willson et al., "The Structure–Activity Relationship between Peroxisome Proliferator–Activated Receptor γ Agonism and the Antihyperglycemic Activity of Thiazolidinediones", J. Med. Chem., vol. 39, No. 3, pp. 665–668 (1996).

Robert C. Anderson, "Carnitine Palmitoyltransferase: A Viable Target for the Treatment of NIDDM?", Current Pharmaceutical Design, vol. 4, No. 1, pp. 1–16 (1998).

Didier Portilla, "Carnitine palmitoryl–transferase enzyme inhibition protects proximal tubules during hypoxia", Kidney International, vol. 52, pp. 429–437 (1997).

Robin E. Buckingham et al., "Perpxisome Proliferator–Activated Receptor–γ Agonist, Rosiglitazone, Protects Against Nephropathy and Pancreatic Islet Abnormalities in Zucker Fatty Rats", Diabetes, vol. 47, pp. 1326–1334 (Aug. 1998).

Thomas P. Burris et al., "A Novel Method for Analysis of Nuclear Receptor Function at Natural Promoters: Peroxisome Proliferator–Activated Receptor γ Agonist Actions on aP2 Gene Expression Detected Using Branched DNA Messenger RNA Quantitation", Molecular Endocrinology, vol. 13, pp. 410–417 (1999).

* cited by examiner

*Primary Examiner*—Sandra Saucier
(74) *Attorney, Agent, or Firm*—Birch, Stewart, Kolasch & Birch, LLP

(57) ABSTRACT

The present invention provides a method for screening or identifying therapeutic or prophylactic agents for renal diseases, which comprises assaying a test substance for the activity of up-regulating the expression of fatty acid-binding protein (FABP), and novel mouse proximal renal tubular epithelial cell lines useful therein. The present invention also provides therapeutic or prophylactic agents for renal diseases comprising, as an active ingredient, an agent having activity of up-regulating FABP expression; agents for up-regulating the expression of FABP, and for treating or preventing renal diseases, which comprise a compound having activity of peroxisome proliferator-activated receptor (PPAR) agonist or carnitine palmitoyltransferase (CPT) inhibitor or the like.

3 Claims, 9 Drawing Sheets

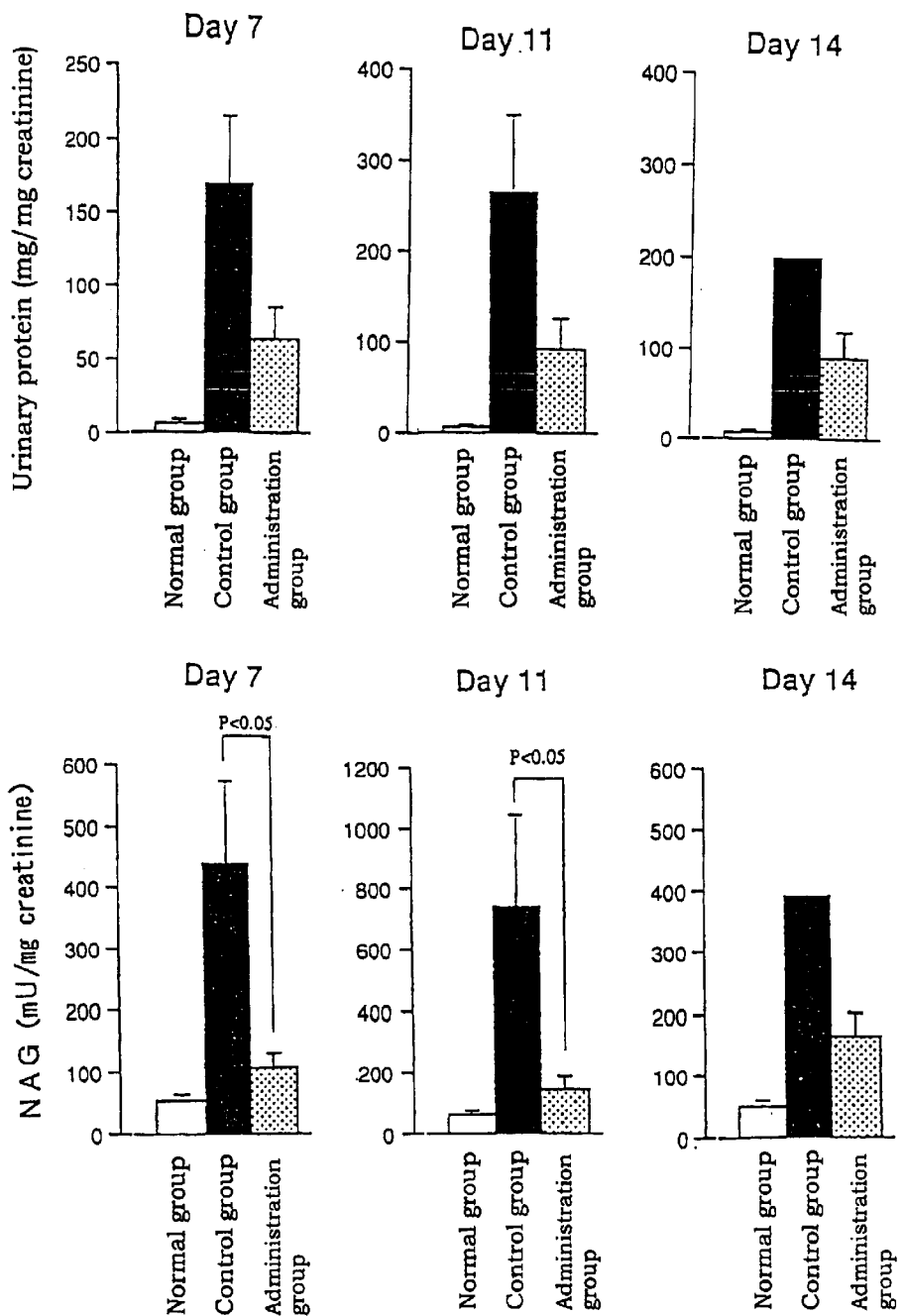

REMEDIES FOR KIDNEY DISEASES AND METHOD FOR SCREENING THE SAME

This application is the national phase under 35 U.S.C. § 371 of PCT International Application No. PCT/JP00/01695 which has an International filing date of Mar. 21, 2000, which designated the United States of America.

TECHNICAL FIELD

The present invention relates to therapeutic agents for renal diseases and a method for screening and identifying the same. In particular, the present invention relates to a method for screening and identifying such agents, which method was established with close attention directed to the expression of fatty acid-binding protein. The present invention also relates to a cell line established from kidney (proximal renal tubule) cells.

BACKGROUND ART

Renal diseases such as nephritis generally presents complex and different pathological aspects, and, when become chronic, may cause serious progression including glomerulosclerosis or interstitial fibrosis, and eventually renal insufficiency. Accordingly, an appropriate treatment in the earlier stage is highly demanded, but there are few therapeutic drugs effective for such purpose. Among the limited number of available drugs, steroids show clear effect but can be accompanied by unacceptably strong adverse side effects. Accordingly, there have been great demands for novel and superior therapeutic agents for renal diseases.

Fatty acid-binding proteins (FABPs) are classified as a group of proteins of molecular weight of around 15 kDa, which present in cytosol and have ability to bind to fatty acids. FABP has been thought to play a role in the regulation of metabolic enzymatic system by transporting and accumulating fatty acids into cells. However, nothing has been known about the correlation between FABP and renal diseases so far.

As for FABP, at least seven molecular species are known, such as liver-type FABP (L-FABP), intestinal-type FABP (I-FABP), heart muscle-type FABP (H-FABP), brain-type FABP (B-FABP), cutaneous/epidermal—type FABP (C-FABP/E-FABP), adipocyte-type FABP (aP2) and peripheral neuron-type FABP (myelin P2). They all have binding activity to fatty acids and considered to be members of a family evolved from a common ancestral gene. Each FABP shows specific histological distribution pattern. The nomenclature of respective FABP means in which organ the FABP was firstly found, but does not necessarily mean that the said FABP exclusively exists in such organ.

In human kidney, at least two FABPs, i.e., liver-type (L-FABP) and heart muscle-type (H-FABP), are expressed and L-FABP is distributed mainly in proximal renal tubule while H-FABP in distal renal tubule (Maatman et al., *Biochemical Journal*, vol. 288, p. 285–290, 1992; Maatman et al., *Biochemical Journal*, vol. 273, p. 756–766, 1991).

The expression and distribution of FABP in kidney of rodents is quite different from that of human. In rodents, L-FABP is expressed scarcely in proximal renal tubule and is distributed in distal renal tubule only in a small amount (Maatman et al., *Biochemical Journal*, vol. 288, p. 285–290, 1992). Predominant FABPs in rodent kidney are H-FABP and kidney-type FABP (K-FABP). H-FABP is mainly distributed in distal renal tubule. K-FABP is thought to be produced as follows. When $\alpha_{2U}$-globulin synthesized in liver is excreted from the circulatory blood to urine in kidney, a portion thereof is reabsorbed by renal tubular cells and converted into K-FABP through the intracellular processing (Kimura et al., *FEBS Letters*, vol. 246, p. 101–104, 1989).

DISCLOSURE OF INVENTION

One of the purposes of the present invention is to provide therapeutic or prophylactic agents for renal disease, which exert effect through a novel mechanism of action, and a method for screening or identifying such drugs. The other purpose of the present invention is to provide a novel cell line useful in the above-mentioned screening or identifying method and the like.

As described above, there had been nothing known about the correlation between FABP and renal diseases before the present inventors found that the decrease in FABP level in urine or renal tissues precedes the infiltration of macrophage or interstitial fibrosis in mouse model of nephritis. The inventors have also found that the L-FABP level in renal tissue is decreased in patients suffering from renal diseases of bad prognosis, and established a method of diagnosing renal diseases based on these findings, which method is focused on FABP (JP-A-11-242026, WO99/27363). The present inventors have continued the research and found that the increase of expression of FABP leads to treatment of renal diseases such as nephritis, in other words, a drug capable of up-regulating the expression of FABP can be a therapeutic agent for renal diseases, and established the present invention.

The present invention provides a method for screening or identifying therapeutic or prophylactic agents for renal diseases, which comprises assaying a test substance for the activity of up-regulating the expression of fatty acid-binding protein (FABP) in animal cells. Further, the present invention provides therapeutic or prophylactic agents selected or identified by such method. Also provided are therapeutic or prophylactic agents for renal diseases comprising, as an active ingredient, an agent having activity of up-regulating the expression of FABP in kidney cells or tissues, for example, a compound having activity of peroxisome proliferator-activated receptor (PPAR) agonist or the like. The present invention also provides a novel mouse proximal renal tubular epithelial cell line useful in the said screening or identifying method.

In patients of renal disease, tissues or cells of kidney are exposed to various kinds of stress such as high proteinuria, ischemia, etc. The therapeutic or prophylactic agents selected or identified by the present method, namely a drug capable of up-regulating the expression of FABP, can protect such cells or tissues. Accordingly, their mechanism of action is based on the protective activity of FABP in kidney tissue or cells (particularly, in renal tubular cells) against stress caused by high proteinuria, ischemia or the like.

Recently, the high proteinuria is regarded as not only a mere indication of renal injury but also one of risky factors per se (Kees-Folts et al., *Kidney International*, vol. 45, p. 1697–1709, 1994; Eddy et al., *Journal of American Society of Nephrology*, vol. 5, p. 1273–1287, 1994). It has been known that albumin, a main component of urine, is generally associated with several free fatty acid molecules. Fatty acids binding to urinary proteins are considered to be reabsorbed from brush border membrane of proximal renal tubular epithelial cells, and intracellularly bound to FABP, transported to mitochondria or peroxisome and undergone β-oxidation. In the absence of sufficient amount of FABP, normal β-oxidization of fatty acids can be hindered, which may stimulates the generation of lipid factors (kidney injury factor) that activate macrophages, and lead to the development of interstitial fibrosis via immunological mechanism. In such a case, enhancement of expression of FABP in proximal renal tubular epithelial cells can normalize the fatty acid metabolism and suppress the generation of lipid factor having renal injuring activity and thereby contributing to the improvement of pathology of renal disease.

BRIEF DESCRIPTION OF DRAWINGS

In FIG. 5, L-FABP antisense refers to LLC-PK1 cells originated from porcine proximal renal tubular cell comprising transiently transfected L-FABP antisense RNA expression vector, and control refers to the same cells comprising transiently transfected vector only.

In FIG. 6, "24" refers to a mouse proximal renal tubular cell line (clone 24) (control cell), and "24-19" refers to a mouse proximal renal tubular cell line in which human L-FABP gene has been introduced and forced to express (clone 24-19).

FIG. 9 shows the results of examination into the effect of a drug (MCC-555) on the proteinuria and NAG excretion in a model-mouse for renal disease (adriamycin-induced glomerulosclerosis model mouse) produced using a transgenic mouse introduced with human L-FABP gene.

BEST MODE FOR CARRYING OUT THE INVENTION

Figure 1:
FIG. 1 is an electron micrograph showing the morphology of mouse proximal renal tubular epithelial cell line No.13 (37-13).

Renal diseases contemplated by the present invention (method of screening or identifying therapeutic agents, and the resultant drugs) includes renal disease such as diabetic nephropathy, glomerulonephritis, nephrotic syndrome, focal glomerulosclerosis, immune complex nephropathy (e.g., IgA nephropathy, membranous nephropathy), lupus nephritis, drug-induced renal injury, renal insufficiency, and the like.

The present invention is applicable to mammals including apes, dogs, cats, pigs, cows, sheep, goats, rabbits, rats, mice as well as humans.

In mammals including human but for rodents, L-FABP and H-FABP are expressed in kidney cells and tissues. L-FABP is distributed in proximal renal tubule and H-FABP distributed mainly in distal renal tubule. To create novel therapeutics for renal diseases, it is important to focus attention to FABP in kidney cells or tissues, especially, to FABP in proximal renal tubular cells, for example, L-FABP in proximal renal tubular cells in the case of human.

The method of screening or identifying therapeutic agents for renal diseases of the present invention can be carried out in the following manner. A test substance can be assayed for the up-regulating activity on intracellular FABP expression (hereinafter, it may be referred to as "FABP up-regulating activity") by culturing animal cells (mammalian cells or tissues) in the presence of the said test substance and comparing the amount of FABP expressed in cells with that expressed in cells cultured in the absence of a test substance. Alternatively, such an assay can be conducted by administering a test substance to animals and comparing the amount of FABP expressed in renal tissues or cells of the animal with that expressed in renal tissues or cells of non-treated animals.

When an increased amount of FABP is expressed in the presence of a test substance (or in administration group), it is determined that said substance has up-regulating activity corresponding to the degree of effect, and can be useful as therapeutics for renal diseases. The screening of therapeutic agents for renal diseases can be conveniently conducted by selecting substances having high FABP up-regulating activity as candidates.

Further, since a candidate substance is assayed for the FABP up-regulating activity and then identified as a therapeutic agent having FABP up-regulating activity, the mechanism of action as a therapeutic for renal disease should be clear. As a result, a therapeutic agent properly characterized can be provided.

Examples of method of detecting FABP expression include a method where the expression of gene is measured by reporter assay using a reporter protein as an indicator. Further, the expression of gene can be detected at mRNA level. In addition, the expression of FABP can be directly detected in cell extract at protein level.

When conducting the measurement of gene expression by reporter assay, for example, a DNA construct comprising a FABP gene transcriptional regulatory region and a reporter gene ligated downstream therefrom is constructed and introduced into an appropriate animal cells. The cells are then cultured in the presence or absence of a test substance and the activity of reporter protein or the like in cell extract can be measured, and thereafter, the expression amounts be determined and compared.

The amino acid sequence of FABP and nucleotide sequence encoding the same have been reported for various species (Veerkamp and Maatman, *Prog. Lipid Res.*, vol.34, pp. 17–52, 1995). For example, the sequence information of L-FABP is known in regard to human cDNA (Lowe et al., *Journal of Biological Chemistry*, vol. 260, pp. 3413–3417, 1985; Genbank/EMBL accession No. M 10050), rat chromosomal gene (Sweetser et al., *Journal of Biological Chemistry*, vol. 261, pp.5553–5561, 1986; Genbank/EMBL accession No. M13501), and the like.

Accordingly, FABP cDNA or chromosomal gene can be obtained from an appropriate DNA libraries by any one of or combinations of PCR method, colony hybridization method, plaque hybridization method and the like using a primer or probe designed on the basis of sequence information as mentioned above.

The reporter construct and reporter plasmid containing the same can be prepared by a conventional gene recombinant technology with a transcriptional regulatory region present in 5' upstream region of FABP chromosomal gene and an appropriate reporter gene.

As a reporter gene, it is preferred to use a gene of an enzyme which is stable and facilitates the quantitative determination of activity, although there are no limitations. Examples of such reporter genes include β-galactosidase gene (lacZ), bacterial transposon-derived chloramphenicol acetyl transferase gene (CAT), firefly-derived luciferase gene (Luc) and the like.

When the gene expression is detected at mRNA level, it can be conducted by, for example, extracting RNA (mRNA) from cells or tissues, and detecting and determining the mRNA transcribed from FABP gene by PCR method (Polymerase chain reaction method) ("PCR Protocols", Innis M A, Gelfad D H, Sninsky J J and White T J eds., Academic Press, Sandiego, 1990), RNase protection assay method (Nucleic Acid Research, vol. 12, pp. 7035–7056, 1984), Northern blotting analysis, or the like.

When the gene expression is detected at protein level, it can be conducted by, for example, immunochemical method (e.g., ELISA, immunohistochemical staining method) using anti-FABP antibody. The antibody can be prepared by a conventional method using purified FABP as an antigen. The distribution among organs, molecular weight, and primary structure of respective molecular species of FABP have been reported (Fujii et al., *Arteriosclerosis, vol.* 24, pp. 353–361, 1996; Veerkamp and Maatman, vol. 34, pp. 17–52, 1995; Drickamer et al., *J. Biol. Chem.*, vol. 256, pp. 3634–3636, 1981; Unterman et al., *Proc. Natl. Acad. Sci. USA*, vol. 78, pp. 3478–3482). Purified FABP can be prepared on the basis of such information. Alternatively, the preparation may be conducted by gene recombinant technology using cDNA isolated on the basis of the known nucleotide sequence of a gene.

When the present method is carried out in vitro using cultured cells, it is preferred to use animal cells (mammal cells or the like). Above all, cells from kidney of animals are preferred, renal tubular cells are more preferred and proximal renal tubular epithelial cells are especially preferred. Cells to be used may be primary cultured cells or immortalized cells (cell lines). Immortalized cells (cell lines) are advantageously used in view of facilitated cultivation and handling.

As human kidney-derived cells, urinary exfoliated cells (specifically, proximal renal tubular epithelial cells) isolated from human urine sample can be used. Cells from human kidney are advantageously used to make prediction of action in human more reliable.

Specific examples of known cell lines from renal tubule include MDCK (ATCC CRL 6253), a cell line derived from canine renal tubule (distal renal tubule), LLC-PK1 (ATCC CRL 1392), a cell line derived from porcine renal tubule (proximal renal tubule), and the like.

In addition to the above, there are immortalized cell lines which the present inventors have established from mouse proximal renal tubular cells as hereinafter described in Example 2, such as mouse cell line mProx 37-13 that was originally deposited at The National institute of Bioscience and Human Technology (1-1-3 Higashi, Tsukuba, Ibaraki, Japan (Accession No. FERM P-16985; date of deposition: Sep. 9, 1998) and transferred to an international deposition (Accession No. FERM BP-7038; date of transfer to international deposition: Feb. 21, 2000) under the provision of Budapest Treaty. These cell lines are characterized by the following properties (1), (2) and (3):

(1) it shows morphology of epithelial cells;
(2) it has ability to uptake albumin; and
(3) it is responsive to the stimulation by parathormone and induced to produce intracellular cAMP but is unresponsive to the stimulation by vasopressin.

Among the above-mentioned renal tubule-derived cell lines, LLC-PK1 does not maintain the property (3) that is characteristic to proximal renal tubular cells in living body, although said cell line is epithelial cells originated from proximal renal tubule. See, Example 2 below. In contrast to this, the cell lines that have been established by the present inventors definitely maintain the entire properties characteristic to proximal renal tubular epithelial cells including responding activity to hormone, and hence the use thereof should make the system more close to the in vivo physiological environment. Accordingly, these cells can be advantageously used to establish an effective method of screening and identifying therapeutic agents for renal diseases.

Test substances identified to have the FABP up-regulating activity according to the method of the present invention can be subjected to further examination using any of known pathological models (in vivo or in virto) to confirm the therapeutic and/or preventive effect.

Examples of in vitro pathological model include a model generating kidney injuring lipid (inflammatory lipid) (Kees-Folts et al., *Kidney International*, vol. 45, pp. 1697–1709, 1994) and the like. Examples of in virto pathological model include models of accelerated anti-GBM nephritis (Nagai, et al., *Jpn. J. Pharmacol.*, vol. 32, pp. 1117–1124, 1982), STZ-induced diabetic nephropathy (Sharma et al., *Diabetes*, vol. 45, pp. 522–530, 1996), puromycin-induced focal glomerulosclerosis (Hirano, et al., *Nephron*, vol. 60, pp. 443–447, 1992), adriamycin-induced glomerulosclerosis (Chen, et al., *Nephron*, vol. 78, pp. 440–452, 1998), cyclosporin nephropathy (Gillum, et al., *Transplant*, vol. 46, pp. 285–292, 1988) and the like.

Examples of drugs found to have FABP up-regulating activity include agonists of peroxisome proliferator-activated receptor (PPAR), carnitine palmitoyltransferase (CPT) inhibitors, and the like. The existence of a peroxisome proliferator-responding sequence upstream from the FABP gene supports the finding that PPAR agonist has up-regulating activity on FABP expression.

Examples of PPAR agonist usable include known PPAR agonists (Lehmann, et al., *Journal of Biological Chemistry*, vol. 270, pp. 12953–12956, 1995; Willson et al., *Journal of Medicinal Chemistry*, vol. 39, pp. 665–668, 1996), and also compounds which are newly confirmed to have activity as PPAR agonist according to a method described in literatures (WO99/10532; WO96/33724; WO96/22884; Mizukami et al., *Biochemical Biophysical Research Communications*, vol. 240, pp. 61–64, 1997; Krey et al., *Molecular Endocrinology*, vol. 11, pp. 779–791, 1997; Buckle et al., *Bioorganic & Medicinal Chemistry Letters*, vol. 6, pp. 2121–2126, 1996; Tontonoz et al., *Genes and Development*, vol.8, pp. 1224–1234, 1994). Above all, MCC-555 (chemical name: 5-[6-(2-fluorobenzyloxy)naphthalene-2-ylmethyl]thiazolidine-2,4-dione; EP604983) is especially preferred as PPAR (PPARγ) agonist.

Examples of CPT inhibitor usable include known CPT inhibitors (*Current Pharmaceutical Design*, vol. 4, pp. 1–15, 1998), and also compounds which are newly confirmed to have CPT inhibitory activity according to a method described in literatures (Saeed, et al., *Arch. Biochem. Biophys.*, vol. 305, pp. 307–312, 1993; Kanamura et al., *Life*

Science, vol., 37, pp. 217–223, 1985; Shinagawa et al., *J. Med. Chem.*, vol. 30, pp. 1458–1463, 1987). Above all, Etomoxir (chemical name: ethyl 2-[6-(4-chlorophenoxy) hexyl]oxiranecarboxylate; EP46590 and *Current Pharmaceutical Design*, vol. 4, pp. 1–15, 1998) and 4-THA (chemical name: 2-hydroxy-3-propyl-4-[6-(tetrazol-5-yl) hexyloxy]acetophenone; Biochem. J., vol. 252, pp. 409–414, 1988) are especially preferred as a CPT (CPT I) inhibitor.

PPAR agonists and CPT inhibitors are known as therapeutic drugs for diabetes. Further, there have been reported that symptoms of renal diseases due to diabetes can be ameliorated with these drugs in pathological models of diabetes (Buckingham et al., *Diabetes*, vol. 47, pp. 1326–1334, 1998). However, this can be attributed to the amelioration of diabetes which is the primary disease and nothing has been taught or suggested that PPAR agonists or CPT inhibitors are applicable to renal diseases not caused by diabetes. To the contrary, the therapeutic or prophylactic agents of the present invention are suitable for application to renal diseases other than those caused by diabetes (e.g., diabetic nephropathy).

When a test substance, an agent having FABP up-regulating activity, a PPAR agonist, a CPT inhibitor or the like is administered to an animal or human, any administration method such as oral, intravenous, intramuscular or subcutaneous administration is available. In addition, it may be formulated together with an appropriate inert carrier depending on the administration form, if necessary. Although an appropriate dosage varies depending on the administration route, age, body weight, conditions of the patient and the like, the daily dosage can generally be determined within range of 1–300 mg/kg for oral administration and 0.01–50 mg/kg for non-oral administration.

The pharmaceutical agents (therapeutics or prophylactics) of the present invention exert their in vivo medicinal action on the basis of the FABP up-regulating activity, i.e., action as PPAR agonist or CPT inhibitor. The pharmaceutical agents of the present invention do not include any drugs lacking sufficient FABP up-regulating activity (or action as PPAR agonist or CPT inhibitor) to render in vivo medicinal effect. Also excluded from the pharmaceutical agents of the present invention are those which exert in vivo medicinal action based on a given main action different from FABP up-regulating activity (action as PPAR agonist or CPT inhibitor). As used herein, the pharmaceutical agents of the present invention do not include those which are inapplicable to treatment or prophylaxis of diseases due to toxicity or inferior natures from the phrmacokinetic viewpoint or the like.

The following Examples are provided to further illustrate the present invention in detail but are not to be construed as limiting the scope thereof.

Throughout the following examples, otherwise mentioned, each procedure was conducted following the teachings in "*Molecular Cloning*, Sambrook, J., Fritsch, E. F. and Maniatis, T. eds., Cold Spring Harbor Laboratory Press, 1989), and the reagents or kits of commercial source were used in accordance with the manufactures protocol.

EXAMPLES

Example 1
Preparation of L-FABP Reporter Plasmid
(1) Isolation of Human FABP cDNA Human L-FABP cDNA was isolated from human hepatocyte cDNA library (Clontech, Cat#HL1115b LOT#5621) by PCR (polymerase chain reaction) method. Primers were designed based on known sequence information (Lowe et. al., *Journal of Biological Chemistry*, vol. 260, pp. 3413–3417, 1985; Genbank/EMBL accession No. M10050) to result in fragment obtained by PCR having BamHI recognition sites at both ends. DNA fragment (about 420 base pairs) resulted from PCR contained the entire human L-FABP cDNA coding region. This fragment was ligated into an appropriate plasmid.

(2) Isolation of Human FABP Chromosomal Gene

Human L-FABP chromosomal gene was cloned from human chromosomal DNA library (Clontech, Cat#HL1006d LOT#5621) by plaque hybridization method using the fragment (about 420 base pairs, BamHI fragment) obtained in (1) above which includes human FABP cDNA as a probe. The resultant clone contained an about 20 kb insert fragment. Partial sequencing showed that this fragment included the entire human L-FABP coding region.

A fragment (about 5360 bp, SalI-kpnI fragment) including the 5' upstream region was excised from the insert fragment, inserted into a vector plasmid and used in the following experimentation. The nucleotide sequence of the fragment (SalI-kpnI fragment) including the 5' upstream region is shown in the SEQ ID NO:1.

(3) Preparation of L-FABP Reporter Plasmid

A fragment (about 100 bp) was obtained by amplifying a region extending from the NspV recognition site (nucleotide No. 4670 in the SEQ ID NO: 1, in the 5' upstream sequence) to the site positioned just before the initiation codon, which is about 100 bp downstream from the former by PCR method using L-FABP gene fragment (about 5360 base pairs, SalI-KpnI fragment) obtained in (2) as a template. Separately, the SalI-KpnI fragment was introduced into the SalI-KpnI site of pUC18 plasmid, and then the resulted plasmid was digested with NspV and KpnI to delete a portion downstream from the NspV recognition site. This plasmid was ligated to the previously obtained PCR fragment to give a plasmid pUC18-9/25.

The resulted plasmid was then digested with SalI and KpnI, and the generated fragment (about 4760 bp) was inserted into vector plasmid pGV-B (TOYO INK) to give a plasmid for reporter assay. The insert fragment contained the sequence corresponding to the portion from nucleotide No. 1 to No.4760 (just before the initiation codon) in SEQ ID NO: 1 with KpnI recognition sequence (6 bp) added at the 3' terminal.

The resulted L-FABP reporter plasmid has the reporter construction which comprises 5' upstream region including transcriptional regulatory region of human L-FABP gene and a luciferase gene (except for promoter region) ligated at the downstream therefrom.

Example 2
Primary Culture and Immortalization of Renal Tubular Cells, and Introduction of L-FABP Reporter Construct Into the Same (1) Isolation of Nephron A nephron was isolated from mouse kidney by microdissection method in the following manner. A mouse was anesthetized with pentobarbital before laparotomy and perfused with 20 ml of cold Hank's buffered solution (HBS) containing 0.1% BSA via abdominal artery. Then, 10 ml of cold HBS containing 0.1% BSA and 0.1% collagenase type 1 was perfused. These perfusion solutions were previously saturated with a gas mixture of 5% $CO_2$-95% $O_2$. Kidneys were then isolated and cut into slice sections of 0.5–1.0 mm thick with Surgical Brade. These sections were soaked into 10 ml of 0.1% collagenase in HBS, incubated at 37° C. for 10 minutes for enzymatic treatment and then washed with HBS twice. A single segment of nephrons was isolated from these slice sections while observing with stereomicroscope under ice cooling.

(2) Primary Culture of Renal Tubular Epithelial Cells

Primary culture of renal tubular cells was performed using the single segment of nephrons obtained in item (1) above in the following manner. The single segment was washed twice with K1 medium (50:50 DMEM/Ham's F-12, 15 mM Hepes, 13.4 mM sodium bicarbonate, 5 µg/ml insulin, 5 µg/ml transferrin, 5 ng/ml selenous acid, 0.05 µM hydrocortisone, 10 ng/ml epidermal growth factor) containing 10% fetal calf serum, seeded into 96-well plate and cultured overnight in the same medium. On the next day, feeder layer ($2.5$–$5 \times 10^3$ cells/well) were added and co-cultured with the single segment. The used feeder layer was mouse renal mesenchyme-derived cell (cell line prepared by isolating cells from mouse kidney with density gradient centrifugation method and subject to immortalization) or mouse NIH 3T3 cell lacking for growth capacity as a result of X-radiation. The used medium was 10% fetal calf serum-containing K1 medium supplied with an equivalent amount of supernatant of cultured feeder layer and HGF (Hepatocyte Growth Factor) (25 ng/ml). Plates used were those pre-coated with 0.1% gelatin. After 4- to 6-day-cultivation, outgrowth of epithelial cells (renal tubular epithelial cells) from the segment was observed under microscope.

(3) Immortalization of Renal Tubular Epithelial Cells

Renal tubular epithelial cells were cultured in the same manner as (2) above.

After confirmation of outgrowth of epithelial cells, the cells were transfected with a plasmid which contains SV40 Large T antigen gene and neomycin resistant gene (the plasmid was made by inserting SV40 Large T antigen gene into a commercially available plasmid pGEM3SRα neo). Transfection was carried out by cultivating the cells for 1–3 hours at 37° C. in a medium to which a mixture of plasmid and TRANSFECTAM (AR BROWN; cationic liposome) was added.

Following the transfection, cells were cultured for 2–3 days, allowed to detach by Trypsin-EDTA treatment and subcultured in 48-well plate, when additional feeder layers (about $1 \times 10^4$ cells/well) were added. After 1- to 2-day-subcultivation, the cells were re-transfected with the same plasmid. Then, the above procedure was repeated as the culture scale was stepwise increased to give immortalized cells. Afterward, the cultivation of resultant immortalized cells was performed using 10% fetal calf serum-containing K1 medium in culture vessel coated with 0.1% gelatin without using feeder cells.

(4) Introduction of L-FABP Reporter Plasmid

The immortalized cells obtained in (3) above were cultured overnight. The cells were then co-transfected with the human L-FABP reporter plasmid (18 µg) prepared in Example 1 above and a hygromycin-resistant gene-containing plasmid (1.8 µg) (pPUR, Clontech, catalogue#6156-1). The transfection was carried out with TRANSFECTAM in the same manner as descried in (3) above.

After transfection, the cells were cultured in a medium (10% fetal calf serum-containing K1 medium) supplied with hygromycin (100 µg/ml). After 6-day-cultivation, the cells were passaged once and cultured for additional 10 days. The resultant hygromycin-resistant colonies were then picked up under microscope. The picked up colonies were seeded into 96-well plate and cultured, whereby several kinds of transformed cell lines (No. 10-No. 19) containing the plasmid introduced were obtained.

These cell strains were then cultured in high glucose-containing Dulbecco's Modified Eagle's Medium (hereafter, "DMEM") (Gibco) supplemented with 10% fetal calf serum.

(5) Morphological and Physiological Analyses of The Cell Line

The cell line obtained in (4) was subjected to analysis to confirm whether or not they have morphological and physiological features of proximal renal tubular epithelial cells, i.e., analysis regarding ability to respond to hormone and to uptake BSA.

Morphological observations of cell lines under a phase contrast microscope revealed that every cell line have pavement configuration characteristic to epithelial cells. Electron microscopic observation of cell line No. 13 revealed that the cell has microvilli at apical side, forms tight junction characteristic to epithelial cells, expresses actin and form hemidesmosome at basolateral side, and further, possesses cell polarity in part. On the basis of these observations, the resulted cell lines were identified as epithelial cells. The electron micrographs of cell line No. 13 are shown in FIG. 1.

It is known that epithelial cells of renal tubule respond specifically to a given hormone at respective segments and induce intracellular cAMP production. For example, proximal renal tubular cells respond only to parathormone (PTH) and not to vasopressin (AVP). On the other hand, collecting tubule cells, Henle's loop cells and the like respond to AVP.

Figure 2:
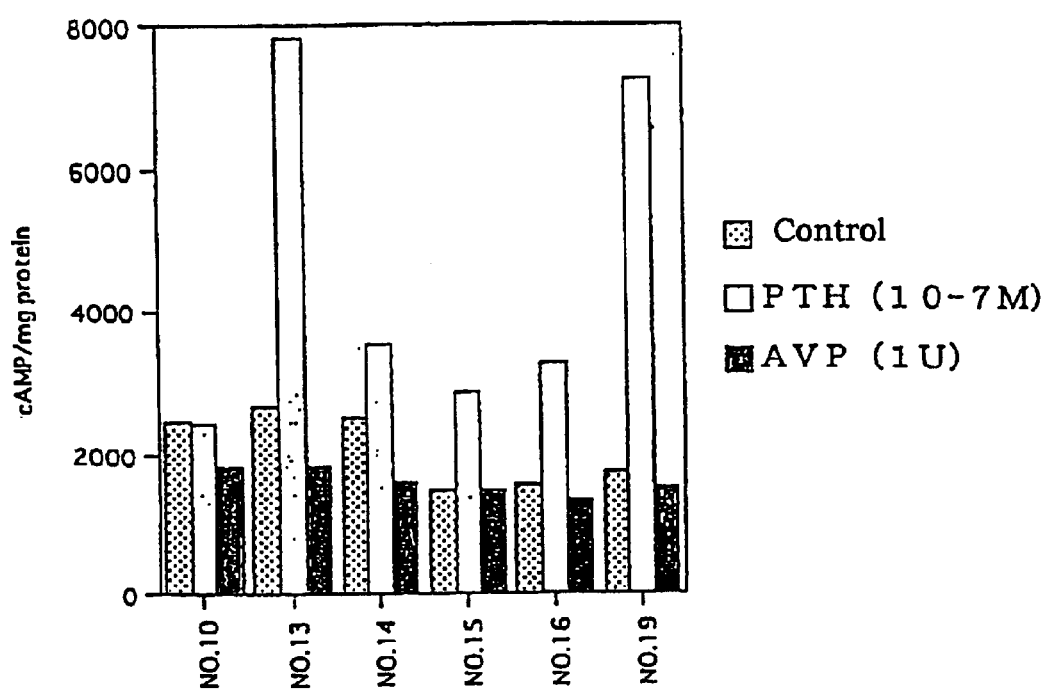
FIG. 2 shows the results of measurement of capability of mouse proximal renal tubular epithelial cell lines (No.10, 13, 14, 15, 16 and 19) in responding to hormonal stimulation (ability to induce intracellular cAMP production upon stimulation with PTH and AVP).

Each cell line (cell line No. 10, 13, 14, 15, 16 and 19) was then tested as to the reactivity to PTH and AVP according to the method described in reference example 1 (6) below. As a result, as shown in FIG. 2, every cell lines except for cell line No. 10 responded to PTH stimulation and, especially, cell line No.13 showed very high reactivity. On the other hand, no cell line responded to AVP. From these results, it was recognized that every cell lines except for cell line No. 10 possess characteristic features of proximal renal tubular cells regarding reactivity to hormone and that cell line No. 13 especially maintains the features well.

A known proximal renal tubular epithelial cell line LLC-PK1 (ATCC CRL1392) was also tested as to reactivity to hormone in the same way as described above. As a result, the ratio of cAMP amounts produced due to hormone stimulation were 1:0.7:7.4 for control: PTH stimulation: AVP stimulation, which showed that said cell line responds to AVP but not to PTH. That is, LLC-PK1, in contrast with cell line No. 13, does not have the feature of proximal renal tubular cells regarding responsiveness to hormone.

Figure 3:
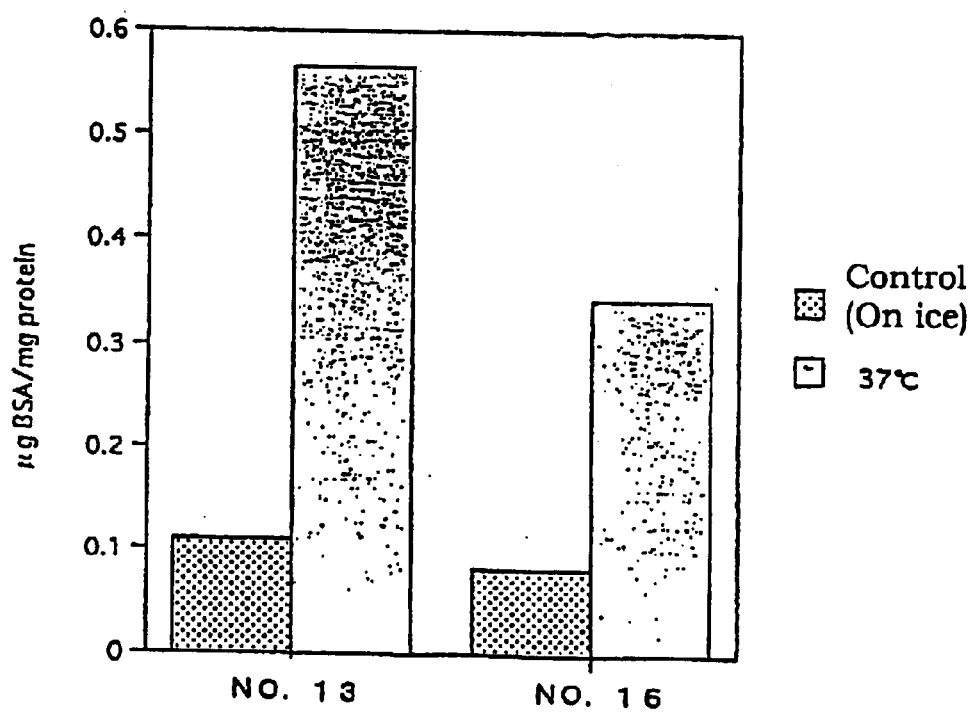
FIG. 3 shows the results of measurement of capability of mouse proximal renal tubular epithelial cell lines (No. 13 and 16) in uptake of BSA.

The cell lines No. 13 and No. 16 were then examined as for albumin uptake activity according to the method described in reference example 1 (5) below. It is known that proximal renal tubule is a segment responsible for reabsorption of protein in filtrate of glomerular filtration and that proximal renal tubular cells are capable of reabsorbing albumin and the like present in plasma in abundance. As shown in FIG. 3, it was recognized that both cell lines have albumin uptake activity. Especially, cell line No. 13 showed about 5-fold enhanced albumin uptake as compared with control, indicating that cell line No. 13 maintains the feature of proximal renal tubular cell such as albumin uptake and the like.

(6) Confirmation of Integrated Region of L-FABP Gene

As described above, cell line No. 13 is a mouse proximal renal tubular epithelial cell line to which an L-FABP reporter plasmid has been introduced. A Southern blot analysis was performed according to the following way to identify whether or not the reporter construct is integrated into chromosome.

If the transcriptional regulatory region of human L-FABP gene from reporter plasmid is inserted without deletion, the chromosomal DNA should give 4.3 Kb fragment upon digestion with restriction enzymes Apa-KpnI. Chromosomal DNA was prepared from cells of cell line No. 13, treated with the restriction enzymes Apa and KpnI and then applied to an agarose electrophoresis. DNAs were transferred to a nylon membrane (Hybond N+ membrane, Amersham) from the electrophoresed gel, and the membrane was washed with 2×SSC and dried. Following prehybridization, the membrane was hybridized at 65° C. overnight in hybridization buffer containing probes, washed with 2×SSC (containing 0.1% SDS) (65° C., 30min) and then subjected to autoradiography. A fragment (1.2 Kb) including 5' upstream sequence of human L-FABP gene was RI labeled and used as a probe.

Consequently, 4.3 Kb fragment was detected and it was confirmed that the transcriptional regulatory region of human L-FABP gene has been integrated without deletion. It was considered that cell line No. 13 contained L-FABP reporter plasmid-derived DNA construct (comprising the human L-FABP gene transcriptional regulatory region and luciferase gene) integrated into chromosome.

This cell line No. 13 (hereafter, referred as "mProx37-13") has been deposited at The National Institute of Bioscience and Human Technology (1-1-3, Higashi, Tsukuba, Ibaraki, JAPAN) with the cell line name "mouse cell line mProx37-13" (Accession No. FERM BP-7038, transfer date to International deposition: Feb. 21, 2000).

Example 3
Assay of L-FABP up-regulating Activity in Proximal Renal Tubular Epithelial Cells A test substance was examined for the L-FABP up-regulating activity by reporter assay method in the following manner using the proximal renal tubular epithelial cell line mProx 37-13 (also referred as "cell line No. 13") comprising L-FABP reporter DNA construct and was prepared in Example 2 above.

Firstly, the cell line mProx 37-13 was added in 96-well flat-bottom plates at $5 \times 10^4$ cells/ 100 μl/well and cultured. The cultivation was conducted using plates pre-coated with 0.1% gelatin and, as a medium, a high glucose-containing Dulbecco's MEM medium (Dulbecco's MEM, high glucose; DMEM) (Gibco) supplemented with 10% fetal calf serum, 100 unit/ml of penicillin and 100 μg/ml of streptomycin. After 48-hour-cultivation, the plate was washed once with serum-free medium, and a serum-free medium containing test substance was added thereto. For control samples, no test substance was added. After additional cultivation, Luciferase activity was detected after 2 to 10 hours.

Luciferase activity was measured in the following way. Cells were washed with phosphate buffered saline (PBS), added 20 μl of solution for cell lysis (LCβ-51, TOYO INK), allowed to stand for 20 minutes at room temperature and then stored at −80° C. overnight. After the plate stored at −80° C. was allowed to become room temperature, 100 μl of luminescence substrate solution (PicaGene luminescence kit, TOYO INK) was added to initiate reaction. Amount of luminescence was detected using luminometer (MicroLumat LP98P, BERTHOLD). The luciferase activity was obtained by integrating the relative luciferase units (RLU) for 10 seconds from the beginning of reaction. The luciferase induction rate (Luc induction rate) was calculated based on the activity value according to the following equation:

Luc induction rate=(test value)/(control value).

Figure 4:
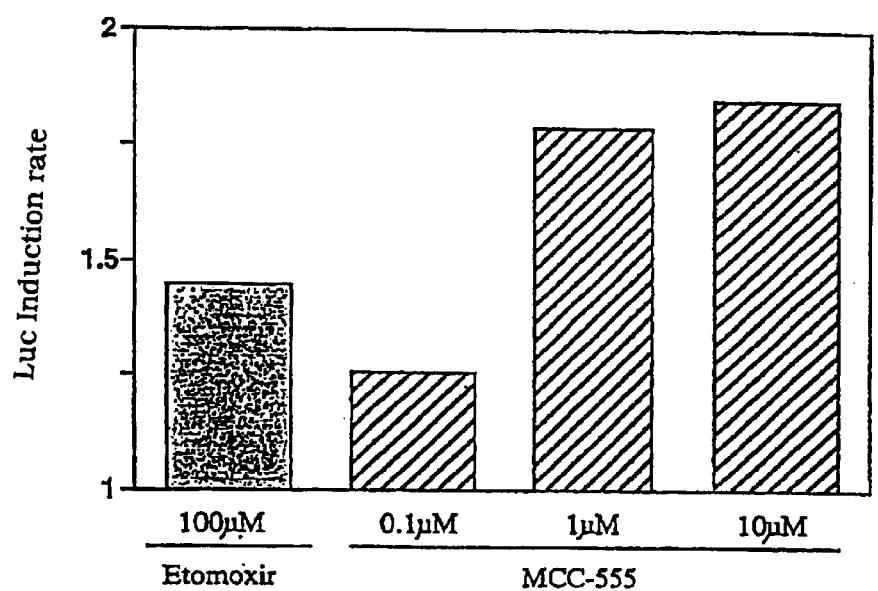
FIG. 4 shows the results of measurement of capability of test substances in up-regulating the expression of L-FABP in reporter assay using mouse proximal renal tubular cell lines.

Induction of luciferase activity was observed when MCC-555, peroxisome proliferator-activated receptor (PPAR) agonist, or Etomoxir, carnitine palmitoyltransferase (CPT) inhibitor, was added as a test substance. These compounds were identified to have L-FABP up-regulating activity. The results of measurement are shown in FIG. 4.

MCC-555 (chemical name: 5-[6-(2-fluorobenzyloxy) naphthalen-2-yl-methyl]thiazolidine-2,4-dione; EP604983) and Etomoxir (chemical name: ethyl 2-[6-(4-chlorophenoxy)hexyl]oxiranecarboxylate; EP46590 and Current Pharmaceutical Design, vol. 4, pp.1–15, 1998) used herein were synthesized according to the method disclosed in the literatures.

Example 4
Assay of L-FABP Up-regulating Activity on Proximal Renal Tubular Epithelial Cells
(Measurements at mRNA Level and Protein Level)

The plasmid isolated in Example 1, (2) above, which contains human L-FABP chromosomal gene (entire length), was linealized and transfected into the porcine renal tubular cell line LLC-PK1 or mouse immortalized renal tubular epithelial cells prepared in a manner similar to that described in Example 2 (3) above to obtain stable transformed cell lines. The human L-FABP chromosomal gene was integrated into these cells on their chromosome without deletion.

Using these cells, L-FABP up-regulating activity of test compounds were examined at RNA level and protein level in the following manner. Cells were cultured to become confluent, when the medium was replaced with serum-free DMEM medium, and test compounds were added to the medium at final concentration of 1 μM. The cultivation was continued at 37° C. Control sample was obtained without adding any test compounds.

Measurement at mRNA level was carried out in the following manner. After cultivation, cells were collected and total RNA was prepared. The resulted total RNA was used as a template for RT-PCR (Reverse transcriptase-Polymerase chain reaction) to detect human L-FABP mRNA. Also, in order to normalize the measurement values, GAPDH (glyceraldehyde 3-phosphate dehydrogenase) mRNA was detected as control in the similar RT-PCR. The resulted PCR products were subjected to agarose-gel electrophoresis, the gel was stained with ethidium bromide to detect bands respectively and the expression amount was determined by densitometry, or visually. As a result, when MCC-555 was added as a test compound, induction of L-FABP mRNA was observed from 15 minute to 24 hour after beginning of cultivation.

Measurement at protein level was carried out in the following manner. Cultivated cells were collected and sonicated and then cell extract was prepared. The amount of L-FABP in the extract was detected by Western Blotting method or ELISA method with anti-human L-FABP antibody. As a result, when MCC-555 was added as a test compound, the up-regulating effect on L-FABP protein expression was observed. The up-regulating effect on L-FABP protein expression was also observed when Etomoxir was added.

Example 5
Assay of L-FABP Up-regulating Activity on Human Urinary Exfoliated Cells
(Assay at mRNA Level)

(1) Isolation of Human Urinary Exfoliated Cell
Renal tubular epithelial cells exfoliated from kidney tissues into urine (hereafter, referred to as "urinary exfoliated cell") were isolated from human urine sample and cultured in the following manner.

Firstly, urine samples from male infant nephritis patients (0–3 years old) were collected using the clean-catch method. The urine samples were then centrifuged (1000 rpm, 10 minutes) at room temperature and the supernatant was discarded. The pellet was washed with 10% (v/v) fetal calf serum-containing Dulbecco's modified Eagle's medium twice and then with culture medium once. The culture medium used herein was a mixture (1:1) of Dulbecco's modified Eagle's medium and Ham's F-12 medium, to which mixture was added fetal calf serum (10% v/v), insulin (5 μg/ml), transferrin (5 μg/ml), sodium selenite (5 ng/ml), dexamethasone ($10^{-8}$ M), nicotinamide (5 mM), penicillin (100 IU/ml) and streptomycin (100 μg/ml).

The pellet was suspended into the culture medium, diluted appropriately and then cultured in collagen type 4-coated dish (3.5 cm in diameter, Falcon). The cultivation was performed under the condition of 5% $CO_2$, 37° C.

The cultured cells were confirmed to be renal tubular epithelial cells because domed form was observed as the cells became confluent and, further, the cells were positive to alkaline phosphatase staining.

(2) Assay of L-FABP Up-regulating Activity

A test compound was examined for the L-FABP up-regulating activity at mRNA revel in a manner similar to that described in Example 4, as shown below.

Firstly, cells were cultured confluently and the medium was replaced with Dulbecco's Modified Eagle's Medium (serum-free) supplied with a test compound at final concentration of 1 μM. Cultivation was continued at 37° C. Test compounds used were MCC-555 (PPAR agonist) and 4-THA (2-hydroxy-3-propyl-4-[6-(tetrazol-5-yl)hexyloxy]-acetophenone) (CPT inhibitor). For control sample, no test compound was added.

After cultivation, cells were collected and total RNA was prepared. The resulted total RNA was used as a template to perform RT-PCR (Reverse transcriptase-Polymerase chain reaction). The resulted PCR products were applied to agarose-gel electrophoresis, the gel was stained with ethidium bromide to detect bands respectively and the expression amount was identified by densitometry or visually. Also, in order to normalize the measurement values, rBAT (related to $b^{0,+}$ system amino acid transporter; Purroy et. al., Genomics, Vol 37. pp. 249–252, 1996) mRNA was detected as control by RT-PCR.

Consequently, as shown in Table 1 below, the amount of L-FABP mRNA expression in human urinary exfoliated cells (human renal tubular epithelial cells) was increased when MCC-555 or THA was added. On the basis of these results, these compounds were identified to have L-FABP up-regulating activity also in human proximal renal tubular cells.

TABLE 1

| Test compound | L-FABP mRNA | rBAT mRNA |
|---|---|---|
| None | − | + |
| MCC-555 (1 μM) | + | + |
| 4-THA (10 μM) | + | + |

Example 6
Effect of Suppression of L-FABP Expression on Cytotoxicity

The effect of suppression of L-FABP expression on cytotoxicity was examined with hypoxia/reoxygenation model (in vitro renal ischemia/reperfusion model) using porcine proximal renal tubule-derived LLC-PK1 cells in the following manner.

Firstly, porcine L-FABP cDNA was cloned by RT-PCR, subcloned in pRC/CMV to obtain antisense RNA expression vector pLFABP-pRC/CMV.

Then, LLC-PK1 cells were seeded in 6-well plate ($1 \times 10^5$ cells/well), cultured for 24 hours and transfected with pLFABP-pRC/CMV using Lipofectamine (GIBCO). As control, cells were transfected with the vector (pRC/CMV) only. These cells were cultured for 24 hours, transferred to an anaerobic chamber (COY) and exposed to hypoxia for 24 hours. Cells were returned to normal atmosphere and reoxygenated for 24 hours, and the cytotoxicity was then measured.

The cytotoxicity was measured utilizing LDH (lactic dehydrogenase) leaked into medium as an index. That is, after hypoxic exposure, the medium was collected and the LDH activity contained in the medium was measured using the assay kit "LDH-Cytotoxic Test Wako" (Wako Pure Chemical Industries, Ltd.)

Figure 5:
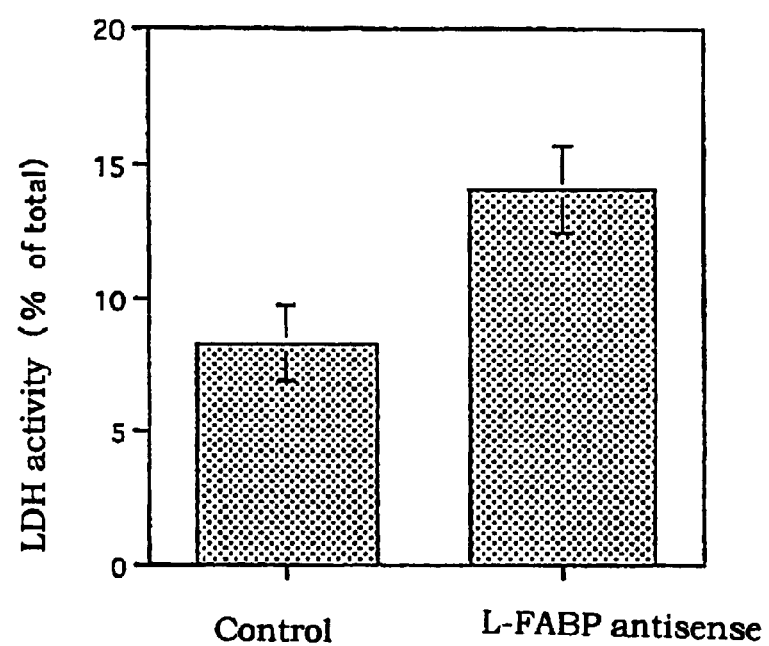
FIG. 5 shows the effect of suppression of L-FABP expression on the cytotoxicity in a model for hypoxia/re-oxygenation (in vitro renal ischemia/reperfusion model).

As a result, as shown in FIG. 5, the leaked LDH activity after hypoxia/reoxygenation was higher in the cells transiently expressing L-FABP antisense RNA than control cells transiently transfected with vector alone, indicating that the former cells suffered more serious injuries.

The fact that the expression of L-FABP antisense RNA, i.e. suppression of L-FABP expression, increased the cytotoxicity during hypoxia/reoxygenation led to a view that L-FABP has a function of protecting cells under a condition that injures proximal renal tubular cells, such as renal ischemia/reperfusion and the like. Example 7

Effect of Imposed Expression of L-FABP on Cytotoxicity

The effect of imposed expression of L-FABP on cytotoxicity was examined with hypoxia/reoxygenation model (in vitro renal ischemia/reperfusion model) using proximal renal tubular cells in a manner similar to that described in Example 6 above.

The plasmid comprising human L-FABP chromosomal gene (entire length) isolated in Example 1, (2) above was linealized and transfected into the mouse proximal renal tubular cells (clone 24) obtained by the same manner as Example 2 (3) to obtain a stable transformed cell (clone 24-19). The human L-FABP chromosomal gene was integrated into the cell on the chromosome without deletion.

The clone 24-19 obtained above and clone 24 as control cell were respectively exposed to hypoxia in an anaerobic chamber (COY) for 24 hours. Cells were returned to normal atmosphere and reoxygenated for 24 hours, and then the cytotoxicity was measured. The cytotoxicity was measured utilizing LDH (lactic dehydrogenase) leaked into medium as an index.

Figure 6:
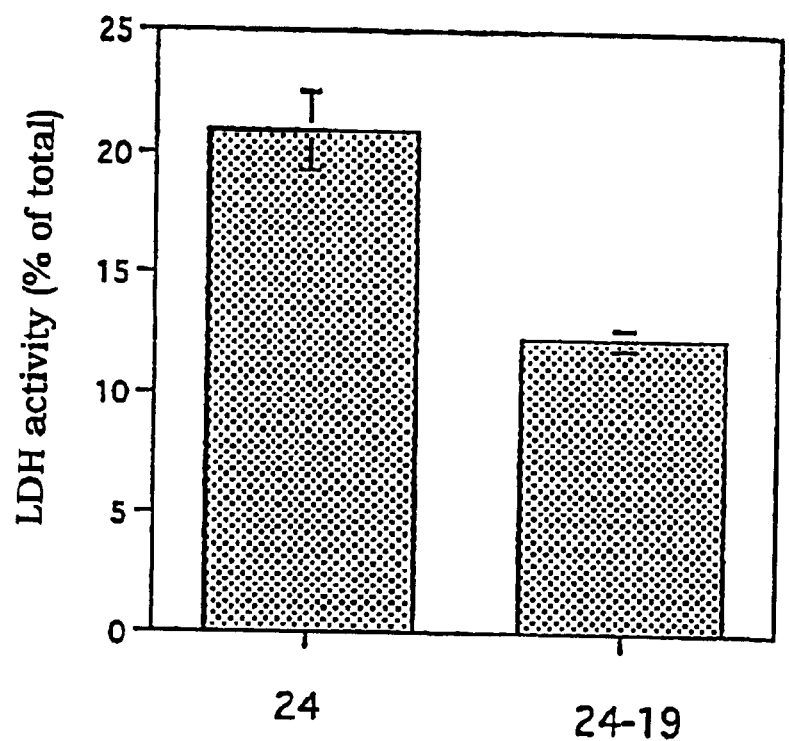
FIG. 6 shows the effect of imposed L-FABP expression on the cytotoxicity in model for hypoxia/reoxygenation (in vitro kidney ischemia/reperfusion model).

As a result, as shown in FIG. 6, the leaked LDH activity after hypoxia/reoxygenation is lower in cells(clone 24-19) introduced with human L-FABP gene to be expressed than in control cells (clone 24), indicating that former cells are more resistant to hypoxia/reoxygenation. The fact that the imposed expression of L-FABP increased the resistance to cytotoxicity during hypoxia/reoxygenation led to a view that L-FABP has a function of protecting cells under a condition that injures proximal renal tubular cells, such as renal ischemia/reperfusion and the like. Example 8

Effects of Drug on Model Mouse of Renal Diseases

An adriamycin-induced glomerular sclerosis mouse was used as a renal disease model to confirm effect of PPAR agonist MCC-555 in the following manner.

An adriamycin(AD)-induced glomerular sclerosis mouse is a pathological model which develops focal glomerular sclerosis in 3 weeks after the onset of nephrosis symptom while showing the symptom and eventually results in irreversible chronic renal insufficiency (Chen et. al., *Nephron*, vol. 78, pp.440–452, 1998). As shown in Examples 3, 4 and 5, MCC-555 is a compound confirmed to have L-FABP up-regulating activity.

In the experiment, 7-week-age female BALB/c mice (purchased from Charles River Japan, Inc.) were used. At the first day of experiment (Day 0), Adriamycin (Sigma) was administered intravenously at 10 mg/kg (10 ml/kg dissolved in saline at 1 mg/ml). Normal group received intravenously an equivalent amount of saline only. To the mice were administered orally MCC-555 or carrier alone for 14 days from the first day of experiment (Day 0 to Day 13). The administration was initially conducted 1 hour before the adriamycin administration, and administration volume was 10 ml/kg for each time.

In drug administration group (n=6), MCC-555 (suspension in 0.1% Tween 80-containing purified water) was administered at a dose of 10 mg/kg to mice that have received adriamycin. In control group (n=6), carrier (0.1% Tween 80-containing purified water) alone was administered to mice that have received adriamycin. Also in normal group (n=3), mice received carrier alone.

Mice were separately housed in "a metabolic cage" and allowed to access food and water ad libitum while collecting urine for 24 hours. Specifically, collection of urine was performed 4 times in total, i.e., day 3–4, day 6–7, day 9–10, and day 13–14. Following measurement of volume, the collected urine was subjected to determination of urinary protein, NAG (N-acetyl-β-D-glucosaminidase) and creatinine (CRE) concentrations by clinical chemistry analyzer (SuperZ-818, NITTEC Co.) After the collection of urine on the last experiment day (Day 14), blood was collected via abdominal aorta under ethereal anesthetization and serum was separated. Cholesterol and albumin were determined using Automated clinical analyzer TBA-80FR (TOSHIBA). Also, kidneys were isolated and fixed with neutral buffered formalin.

Figure 7:
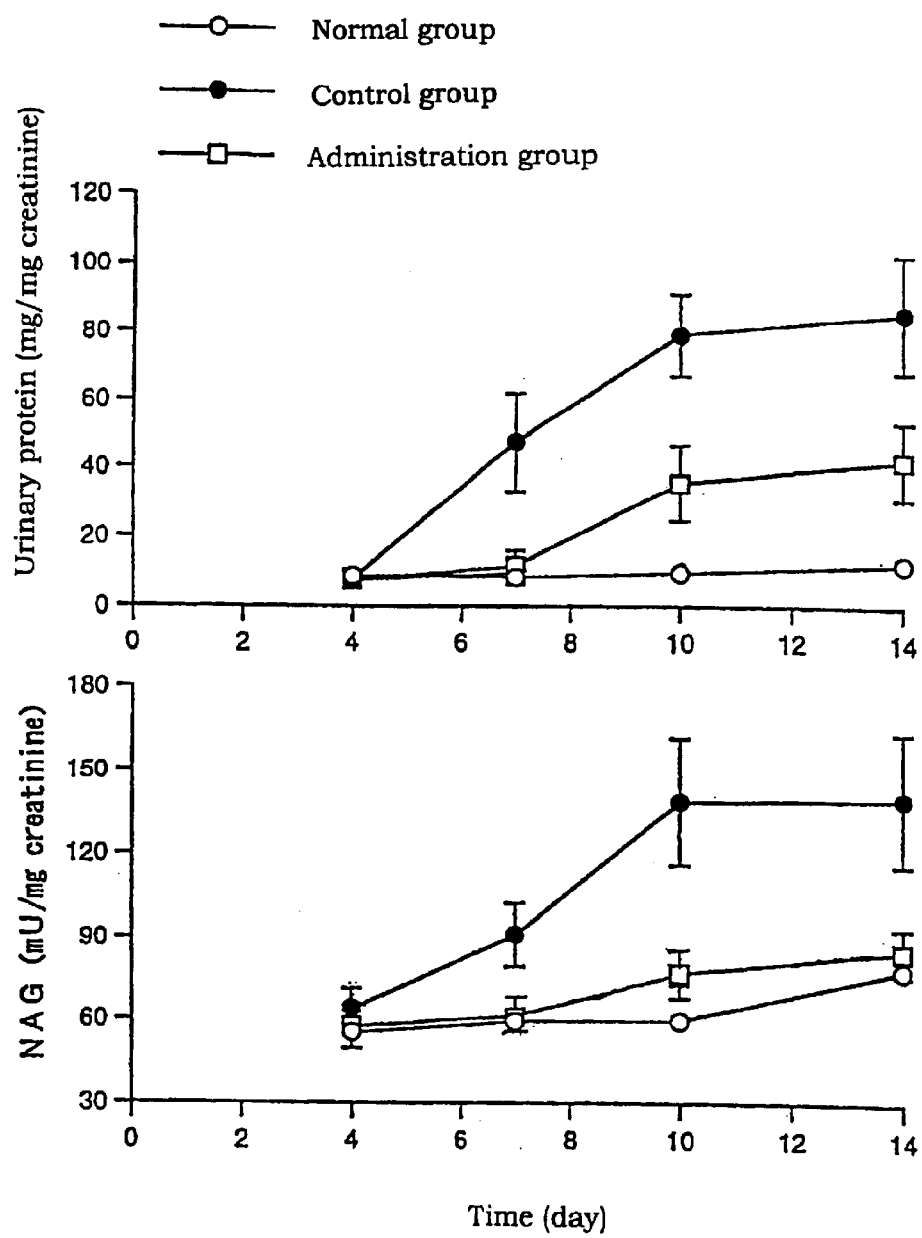
FIG. 7 shows the results of examination into the effect of a drug (MCC-555) on the proteinuria and NAG excretion in a model mouse of renal disease (adriamycin-induced glomerulosclerosis model mouse).

The results of experiment are provided in FIG. 7. As shown in FIG. 7, in control group, urinaxy protein and NAG excretion amount that is an index of proximal renal tubular injury were increased at 7 to 14 days after AD administration. In contrast with this, in drug administration group, the increase of urinary protein and NAG excretion amount were significantly suppressed.

Figure 8:
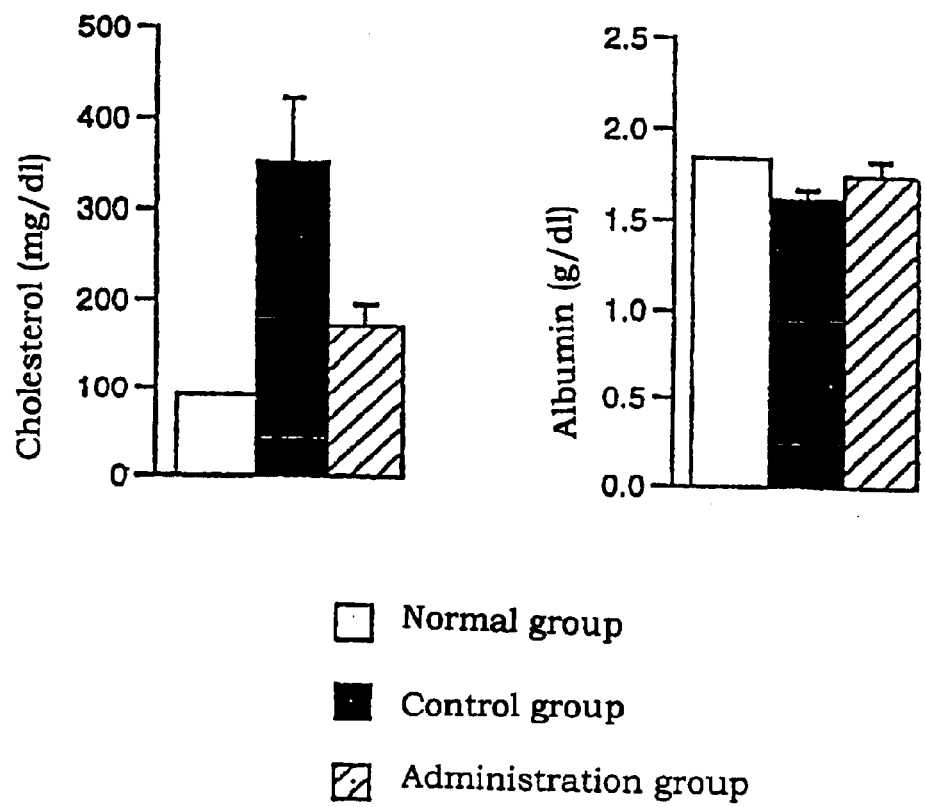
FIG. 8 shows the results of examination into the effect of a drug (MCC-555) on the blood biochemical parameters (blood cholesterol and albumin level) in a model mouse of renal disease (adriamycin-induced glomerulosclerosis model mouse).

The results of blood biochemical examination at Day 14 are provided in FIG. 8. As shown in FIG. 8, hypercholesterolemia and hypoalbuminemia were recognized in control group, which are main symptoms of nephrosis. In contrast with this, such symptoms were improved in drug-administration group.

As described in above, MCC-555 suppressed NAG excretion that is an index of proximal renal tubular injury, and also improved proteinuria, which is main symptom of nephrosis, and blood biochemical examination parameters in renal disease model mouse (adriamycin-induced glomerular sclerosis model). Furthermore, it was confirmed that MCC-555 also inhibited histological changes of kidney in the same model mouse by tissue imaging examination.

Example 9

Effects of Drug on Renal Disease Model of Transgenic Mouse Introduced with Human L-FABP Gene Transgenic mouse (hFABP-Tg mouse) introduced with human L-FABP gene was prepared. The hFABP-Tg mouse was used to make renal disease model similar to that of Example 8 and the effect of MCC-555 was identified.

In the preparation of hFABP-Tg mouse, male BCF1 mouse (13-week or over) was used for sterile mating and natural mating; female ICR mouse (10-week or over) for embryo transplant and as a foster mother; male BDF1 mouse (13-week or over) for mating; and female BCF1 mouse (8-week or over) for collection of eggs, respectively. The resultant transgenic mouse (B6C3F1 line) was used to backcross with BALB/c mouse.

The resultant female transgenic mouse was used to prepare a renal disease model (adriamycin-induced glomerular sclerosis model) and to confirm effects of drug (MCC-555). The preparation of disease model and confirmation of effect of a drug were conducted in a similar manner to that described in Example 8 above except that the dose of adriamycin on the first experiment day (Day 0) was 15 mg/kg (15 ml/kg, dissolved in saline at concentration of 1 mg/ml).

In drug administration group (n=5), MCC-555 (10 mg/kg) was administered to mice that have received adriamycin, and in control group (at the beginning of experiment, n=5), only carrier was administered to mice that have received adriamycin, In normal group (n=3), mice that were not treated with adriamycin received carrier. Collection of urine was performed 3 times in total, i.e., day 6–7 day (Day 7), day 10–11 (Day 11), and day 13–14 (Day 14) and urinary protein, NAG and creatinine concentrations were determined by Automated clinical analyzer after measurements of urine volume.

The results of experiment are provided in FIG. 9. As shown in FIG. 9, in the control group, urinary protein and NAG excretion amount were increased after AD administration, whereas, in drug (MCC-555) administration group, such increase was significantly suppressed. Further, in the control group, 3 animals died during the experiment but in drug (MCC-555) administration group, no animals died.

Reference Example 1

Isolation of Proximal Renal Tubular Epithelial Cells by Density Gradient Centrifugation Method and Primary Culture Thereof (1) Isolation of Proximal Renal Tubular Cells Renal cortical cells were isolated from mouse kidneys in the following manner according to density gradient centrifugation method described in Vinay et. al., *American Journal of Physiology*, vol. 241, F403–F411, 1981.

Two mice were decapitated and bled, and the kidneys were isolated and washed with cold Hank's buffered solution (HBS) and then capsula was removed. Only the cortex was then excised from capsula and cut into 1–2 mm cubic. The sectioned tissues were washed with HBS briefly, and 5 ml of collagenase type 4 solution in HBS (400 µg/ml) was added. The mixture was incubated at 37° C. for 30 minutes. After stirring for 5 minutes, the mixture was filtrated thorough nylon mesh (100 µm) to remove tissue aggregates and washed with HBS. One ml of HBS was added and pipetted briefly to prepare the cell suspension.

The resultant cell suspension was layered on 30–50% Percoll gradient solution and centrifuged (3,500 rpm, 4° C., 30 minutes). After centrifugation, cells separated into each layer (4 layers from the top, fractions 1 to 4) of Percoll density gradient were recovered carefully.

(2) Alkaline Phosphatase Staining of Separated Cells

In the case of kidney, alkaline phosphatase is known to be located in proximal renal tubule. Accordingly, a portion of cells in each layer recovered in (1) above were harvested and stained with alkaline phosphatase as described below. That is, the cell suspension was centrifuged, immobilized on preparation, stained with alkaline phosphatase substrate kit (FUNAKOSHI) and then embedded into glycerol. As a result, the uppermost layer (fraction 1) showed the highest alkaline phosphatase positive rate and hence was considered to be highest in the content of proximal renal tubular cells.

(3) Primary Culture of Proximal Renal Tubular Epithelial Cells

The cells of fraction 1 described in (1) above were treated with collagenase as described below and then primary-cultured. That is, the collected cells were washed once with HBS and treated with enzyme by adding 1 ml of a collagenase type 4 solution (2 mg/ml in HBS) and incubating at 37° C. for 5 minutes. After washing twice with HBS, incubation was continued.

It is generally known that the primary culture of epithelial cells is contaminated with fibroblasts. Accordingly, it is necessary to inhibit the growth of fibroblasts while propagating epithelial cells selectively. To this end, for the cultivation, a combination of (i) MEM/D-Val medium (wherein L-valine was replaced with D-valine in MEM medium; Gibco) supplemented with fetal calf serum, which selectively inhibit the growth of epithelial cells and (ii) serum-free K1 medium, which contains hormones and growth factors capable of specifically propagating epithelial cells, but lacks factors participating in the growth of fibroblasts (50:50 DMEM/Ham's F-12, 15 mM Hepes, 13.4 mM sodium bicarbonate, 5 $\mu$g/ml insulin, 5 $\mu$g/mil transferrin, 5 ng/ml selenous acid, 0.05 $\mu$M hydrocortisone, 10 ng/ml epidermal growth factor) was used in the following manner.

First, the cells were cultured in MEM/D-Val medium containing 10% fetal calf serum for 1 to 2 days. After the confirmation of adhesion and growth of cells, the medium was replaced with serum-fee K1 medium, and the cultivation was continued for about 1 week. The cells were seeded into plates pre-coated with 0.1% gelatin and cultured within $CO_2$ incubator.

(4) Morphological Analysis of Cells

When the cultured cells described in (3) above were observed under a phase contrast microscope, cell growth with pavement configuration was recognized. Further, when the cells became almost confluent, the domed forms were recognized. These observations suggest that the intra-epithelial water and solute transport being performed. From these facts, it was confirmed morphologically that the resulted cultured cells were renal tubular epithelial cells.

(5) Albumin Uptake Activity

It has been known that the proximal renal tubular cells have albumin uptake activity. The cultured cells described in (3) above were examined for albumin uptake activity in the following manner. Cells were cultured to become confluent in 10 cm dish, when the medium was replaced with MEM/D-Val medium and the cells were cultured overnight. Bovine serum albumin (BSA) was then added to the medium at the final concentration of 50 mg/ 10 ml and the cultivation was continued at 37° C. for 90 minutes. As control, cells were incubated on ice in the same medium containing BSA. After cultivation, the cells were washed with phosphate buffered saline (PBS) (pH 7.4) and recovered. These cells were suspended into 200 82 l of PBS (pH 9.6) containing protease inhibitors and sonicated. To the sonicated solution was added PBS (pH 6.4) to adjust pH within the neutral range, and the solution was centrifuged at 12,000 rpm for 15 minutes and the supernatants were collected as cell extracts. The resulted cell extracts were assayed for the presence of BSA by ELISA.

In the ELISA method, anti-albumin antibody (rabbit polyclonal antibody, Sigma) was used as the primary antibody and biotin-labeled anti-albumin antibody was used as the secondary antibody. The primary antibody was absorbed onto 96-well immunoplates. After addition of the cell extracts (100 $\mu$l/well), incubation was conducted at room temperature for two hours. To the well was added diluted secondary antibody and incubated at room temperature for two hours. After washing the wells, color detection was conducted with a detection kit (Vector laboratories, VectorStain ABC-PO kit) containing streptavidin and biotin-labeled horseradish peroxidase.

As a result, the BSA uptake was recognized to be 2.3-fold when cultivation was conducted at 37° C. with addition of albumin compared with control. It was confirmed that the cells have physiological functions of proximal renal tubular cells.

(6) Responding Activity to Hormone

The proximal renal tubular cells are known to be responsive to parathormone (PTH) and induced to produce intracellular cAMP but unresponsive to vasopressin (AVP). The cultured cells described in (3) above were used in the examination of responsiveness to hormone in the following manner.

The cells were cultured to confluent in 24-well plate, when the cell surface was washed with a medium (MEM/D-Val medium) twice. To the cell was added a medium supplied with either PTH ($10^{-7}$ M) or AVP (1 U/ml), and IBMX (3-isobutyl 1-methylxanthin; cAMP phosphodiesterase inhibitor) ($10^{-4}$ M). For control, a medium supplied with IBMX alone was added. After incubation at 37° C. for 10 minutes, cAMP in cells and in medium was extracted with 65% ethanol. The amount of cAMP was determined by ELISA (cAMP EIA system kit, Amersham).

As a result, approximately 1.6-fold intracellular cAMP was recognized in the case of PTH stimulation compared to control. From this observation, it was confirmed that proximal renal tubular cells were contained in the primary culture. Further, in the case of AVP stimulation, approximately 4.6-fold cAMP was recognized compared to control, which indicated that cells originated from sources other than proximal renal tubular cells might be blended.

Sequence Listing Free Text

Free text of SEQ ID NO: 1

<223> GATA signal (GATA_signal)

<223> peroxisome proliferator responsive element (PPRE)

<223> hepatic nuclear factor (HNF) binding-site

<223> hypoxia inducible factor (HIF) binding-site

INDUSTRIAL APPLICABILITY

According to the method of the present invention, it is possible to screen novel therapeutic and/or prophylactic agents for renal diseases precisely and efficiently. Further, such therapeutic and/or prophylactic agents identified and characterized according to the present method (i.e., therapeutic and/or prophylactic agents of the present invention) are useful as excellent therapeutic and/or prophylactic agents for renal diseases of which mechanism of action is definite. In addition, the novel cell line of the present invention maintains well the physiological properties as proximal renal tubular epithelial cells and are useful in various aspects such as research and development of therapeutics for treating renal diseases or the like.

What is claimed is:

1. A method for screening or identifying therapeutic or prophylactic agents for renal disease, which comprises assaying a test substance for the activity of up-regulating the expression of liver-type fatty acid-binding protein (L-FABP) in animal cell, wherein said assay comprises the following steps:

(1) culturing animal cell in the presence or absence of the test substance; and comparing the amount of L-FABP expressed in the cell in the presence of the test substance with the amount of L-FABP expressed in the cell in the absence of the test substance; or (2) administering the test substance to an animal and comparing the amount of L-FABP expressed in renal tissues or cells of the animal with the amount of L-FABP expressed in renal tissues or cells of a non-treated animal, wherein the animal cell is kidney cell or tissue.

2. The method of claim 1, wherein the animal cell is proximal renal tubular cell.

3. The method of claim 1, which further comprises a step for assaying an activity of a test substance by reporter assay using a cell to which a DNA construct comprising a L-FABP gene transcriptional regulatory region and a reporter gene ligated downstream therefrom is introduced.

* * * * *

SEQUENCE LISTING

<160> NUMBER OF SEQ ID NOS: 1

<210> SEQ ID NO 1
<211> LENGTH: 5357
<212> TYPE: DNA
<213> ORGANISM: Homo sapiens
<220> FEATURE:
<221> NAME/KEY: CDS
<222> LOCATION: (4767)...(4835)
<221> NAME/KEY: intron
<222> LOCATION: (4836)...
<221> NAME/KEY: TATA_signal
<222> LOCATION: (4691)...(4697)
<221> NAME/KEY: misc_signal
<222> LOCATION: (4136)...(4141)
<223> OTHER INFORMATION: GATA_signal
<221> NAME/KEY: misc_binding
<222> LOCATION: (4654)...(4659)
<223> OTHER INFORMATION: peroxisome proliferator responsive element (PPRE)
<221> NAME/KEY: misc_binding
<222> LOCATION: (4661)...(4666)
<223> OTHER INFORMATION: peroxisome proliferator responsive element (PPRE)
<221> NAME/KEY: misc_binding
<222> LOCATION: (4544)...(4551)
<223> OTHER INFORMATION: hepatic nuclear factor(HNF) binding-site
<221> NAME/KEY: misc_binding
<222> LOCATION: (3758)...(3765)
<223> OTHER INFORMATION: hypoxia inducible factor(HIF) binding-site

<400> SEQUENCE: 1

```
gtcgactgca gtcaacggat cctctccrty ctctvacccct caccctcaac tacgcccag      60 tgtctgttgt tccctacta gtatccatgt gttctcattg tttagctccc acttataagt      120
gagaacacac agtatttaat tttctgttcc tgtgttcgtt tgcttaggat aatggcctct     180
agctccatcc acgttgctgc aaaggacatg atctcatgct tttttatggc tgcatcatat     240
tccatggtgt atgtatacca cgctttcttt attcagtcta ctgttggtgg gcattaggtt    300
gattccatgt ctttgctatt gtgaataatg ctgcaatgaa catactcatg catgtgtcct     360
tatggtagaa caatttatat tcttttgggc atatacccag tagtgggact gctgggtcaa     420
atggtaattc tgttttaagt tcttttgagga atcaccacac tgcttttccac aatggctgaa   480 ttaattcaca ctctcaccag tagtctgaaa tgttccttttt ctctgcaacc ttgccagcat    540
gttatttttt gacttttaat agtagccatt ctgactggtg tgtgatagta tctcattgtg    600
gttgtgattc gtttacgcaa ttatttcaca aggcaaaaaa tgttgtgacc atttaacaga    660
taagcaagta gaggctcacc aaggctccac atcaggtata agaagagct gggcccaaac     720 ccaagtcctt tccctctgca gccctgcctg tagcagaatt atgggctcct cgggccacct    780
cctatgttca aaacacccag gaaatgggca ggctggcatt gcaggcactg aggtcaaagg    840
cgcttgttct aaaatgaaca cctgtcatat cctggccacc aagaggtgac tcccctcctt    900
tcccacacct gcacgctgcc cgtctgagta gggatgtgag aagagggat gtctagtgtg    960 gagtgagcag ggccagaatc tttggacact ccaaagctgt gcccacagag tgggagtctc   1020
tttttttctt tcttgaaagc cacttgaact ttgtcattgc aattaagctt atctcttctt    1080
gtgtttgctc agctagtggg tggaagatgt cattaccctc tcctaacttt atggaaaact   1140
catgagtatt agttttttgaa atggctactg atctctgtgc cctcaagatt cacacacaca   1200
caaaaaaaaa gacaaaggga agtcatcggg ggttgcctaa gaatggccat atctcagacc   1260
tgggggagag ggggagtcct ggcctggcgt tgatcagctc aatttacttg tcaggctgcc   1320
```

-continued

```
catctgccag ggaaactgtc aaggcttcac tggttgtgcc aggcccttga ccaacctctg   1380
ggtcagctgc attcccaatg ctgttctgag tctgcagcgt tgcctggaca gggtaggcag   1440
gaagtgcagg gtgaggcaga gtggtccaca aggagacagc tcatgggtcc tgctgttcct   1500
cagacaccag gaaaggtgca cctggtccct acttcacctg aggcctccgg ggttggtgct   1560
gacttgctct atggagaagc tttcatgacg ctccttccca ctcccctccg tagatcccag   1620
aaagcagcag tgtgggcat gatacttgac atttgcgatc aaggggagag ggcctagttg    1680
tggaatgtat aagccagaca tccctttatc tgagcgggat gtcaggcagg cagctggggg   1740
catgagataa catgggcact tggagcagat tctcccaaac gaagcaactg atgggtgtga   1800
tgggagttgg gcatggtaat gactctatca cggtcatttt cctcggtgat tatttcattg   1860
attttaggct gcaaaactcc taagctcccc atctaagcaa gtgtttacgt attccttcct   1920
tgacaaatgc tagaagagct ctttaggtag gtagtgaata ggatctcagg tatagagctg   1980
aatttagccc tgggctgaac cttcacatgg tcattagaca gacatatgcc agctattggt   2040
gcaggcttta ggtgtcacat gtaacccaga aggatctaaa taaatgacc ttgaattcct    2100 ccaaagccct tcctaggatg tctagggacc tggggaaccc tgtagggaat gcatcccac    2160 agacactcca cttcctgcag tctgggggag ggacaggaag acacacccag cctctcctgg   2220
tctcctgcat gagggagctg cccttctctt ggtactgctt ctgcatgtgc catctcagcc   2280
tcatcacatc catccagaaa taaagctcag ccttgcatca ttttccactt gctcacatat   2340
tgattcaggc actatatttt actgaagctt ttgaaatagt tggggtggaa attaaagaaa   2400
gatggatggg gattcactgc agcaaatgag cagcttcaaa gccaatgcca tcctggagct   2460
cctttctgca gtctggggga gggacaggaa gacacaccca gcctctcctg gtctcctgca   2520
tgagggagct gcccttctct tcaccagctt ggctctcgct gacacacggg tctgaggtct   2580
ggggtctcac acactctgtc tcccaggcag ctaatccagt catttacaca cacacacaca   2640
cacacacaca cacacacaca cactaggaat tctcatgcca gttcttaaga caatggattt   2700
tttacttcct tgcatataca aaatgaaaa atcagcatcc catctggaga ccagggtcta    2760
atatggaccc ctttagtaca atagacatgt taaagatgt ataatcaaag ctcagagcaa    2820
gatgagagaa ggactgtggg tgtgcccata cttctttgag ccacctcgcc ccttcctgcc   2880
cgctgttcag gtagtcgtgg tgattataaa aagccataag ttctcagcat gcaggcccac   2940
ttcgcttgct gcagggacag ccccaattca tggcctggga ggcaccttgt gtcctagaca   3000
ctgtcagagg agggccaagc agggagggcc agagcacccc tctgtgctgg agggaaaggt   3060
ctgctggtgc cagaatctgc atggcaggac actccattag tgagtgttct ctgcccacag   3120
tgctccaaag gtgaggacct ccctgtggca gggtacacct taacaccacc tgtcagggat   3180
gctgtagaag gaccctggca ctgggactgt ggtggagga gagaacttct gaagtgcttt    3240
gctggatcaa catgtccaaa tgctggagac cacggagggc agagagagtg gcatggacgc   3300
ccccgatgtg tccacttggc cctgtggctg gaactgtggc ttgaggagaa ggaaggaaaa   3360
aggatggaaa ggtagactgg agttgccttt tgagggctgg cagccctgct agaagtttag   3420
gcaatgggag tcattttcca agccaaaaat tagaactcat gatagggaaa tggaagtgtt   3480 attggggtg gccatcatga cccgtcacgt gacactaggc catccaggac ctgtggcctc    3540
tgaagtgatg ggaaccactg aggctcatgc ctggagcagt ggcccgactc agcctatgct   3600
tcaggatgat ctgtctaacc acagagtaga ggaggcccag aggatgaagg ctggaggctg   3660
```

-continued

```
caggtgaaaa ggttgacgcc aaagtccaga caaagaaggg agagaatcta ggggtgaggg    3720
ggtgcttgta aagagctgcc tcagaggcag gaactgggac gtgcacccat tgggcaccac    3780
gcctctctgt gcttcacaac aaactggcac atcccaaggc cactggaagc cctgctgggc    3840
catctcccca aggccagtgc tgtacacata accctacaag accagtttcc tacacataac    3900
cctacaagac cagtttccta cacataaccc cagatccctt gtcctgtctt ctcagtgggg    3960
ctggagcaag tcagcaggtg ccactttctc ctgccttgtc tctgcctaat aaaatgcgtc    4020
tcaatgtttt acacctgcca tttagcatgg actgctttaa cacctcaaaa aggcctgtgg    4080
aggagcctat aatcatcaag gaggaattcc cagaatacaa aataacacta gcggctgata    4140
acaactctaa aaaataagtt tgtgtaataa tgggggtgag aagagatcat aaggttatgt    4200
aaataaggtg aggttttgag ttcaaaggaa ttctctggta tttttctgtg tgtgtacaca    4260
tgcacccaca cacttgtgtg tatatgtgta cagacatata taaacacatg catataatgt    4320
gtatatatgc attacatata tgcacattca tacatcttta tgtacaaaat acatatatgt    4380
atatataaac accgatgtac aaacacatac gcacacatct atatacatac acatgtgtgt    4440
gcacatatac acatacctgc atatacacac atttcgtggg gtgcggagag tcacttaaag    4500
gctgcagggc cataaggctt cctgcttgac tgatattcat taatgtttgc tgaattacag    4560
caaacctttg ctgtgcccat cctgttcttt atcattgacc attgctctca ggagttaatg    4620
tttgaacctg gccataaagg aatcaacagc tgctgacctc tggccgctat tcgaagggaa    4680
gggagccccc tataaaacag cctacagtgg acagtctggt cggcagagcc gcaggtcagt    4740
cgtgaagagg gagctctatt ggatccatga gtttctccgg caagtaccaa ctgcagagcc    4800
aggaaaactt tgaagccttc atgaaggcaa tcggtgagtg ctggactgaa aggcaaagct    4860
gtgggtcaca tcagtgaggg tctagctcta ccagcagtgg ctatttaggg tccaaatgtt    4920
gagatggggg gagagattca ggctatatac acaaactagg gggcatttta ctgacttctg    4980
gagttatttg cagcaagtcc tcactgcaca aggccacccc ataggcaagt ggaaagagca    5040
ctgaactagg gtgtggtctg gattgatggc catgtcattg gcacttcgtt gtgtgatcct    5100
attcctgcat ttattcattc ttcaaacaaa cagtgattca aggccaacca cacactgagc    5160
actgtgctgg atagatacca gggagacaga tgataaaggc aataaggcat tttcttatca    5220
gggaagagaa gagaagaaat aaaggtaata aggcattccc tcaggtgtat ggagcgctga    5280
ctgtgccagg cgactgtgct gaccatggga tatgcaatac cccatctatt ccttgccaaa    5340
aaactaagct gggtacc                                                  5357
```